United States Patent [19]

Hodges et al.

[11] Patent Number: 5,223,604
[45] Date of Patent: Jun. 29, 1993

[54] PSEUDOMONAS EXOENZYME S PEPTIDE COMPOSITION AND METHOD

[75] Inventors: Robert S. Hodges, Edmonton; Randall T. Irvin, Sherwood Park; William Paranchych, Edmonton; Pamela A. Sokol; Donald E. Woods, both of Calgary, all of Canada

[73] Assignee: S.P.I. Synthetic Peptides Incorporated, Canada

[21] Appl. No.: 721,759

[22] Filed: Jun. 25, 1991

[51] Int. Cl.$^5$ ............... A61K 39/02; A61K 37/02; C07K 7/00; C07K 15/00
[52] U.S. Cl. ................ 530/327; 530/326; 530/300; 424/92
[58] Field of Search .......... 424/88, 92; 530/300, 530/326, 327

[56] References Cited
PUBLICATIONS

Doig et al Infect & Imm 58: 124–130 Jan. 1990.
Irvin et al Inf & Imm. 57: 3720–3726 Dec. 1989.
Sokol, P. A. et al., D. E. Microbial Pathogenesis 8:243–257 (1990).
Woods, D. E. et al., Infect. Immun. 55,3:579–586 (1987).
Woods, D. E. et al., J. Med. Microbiol. 26:133–141 (1988).
Woods, D. E. et al., In N. Hoiby, S. S. et al., (ed.) *Pseudomonas aeruginosa* Infection. Antibiot. Chemother. 42:27–35 (1989).
Irvin, R. T. et al., Microbial Ecology Health Disease 3:39–47 (1990).
Grimwood, K. et al., Antimicr. Ag. Chemother. 33,1:41–47 (1989).
Grimwood, K. et al., J. Antimicr. Chemother. 24:937–945 (1989).
Doig, P. et al., Infect. Immun. 56,6:1641–1646 (1988).
Doig, P. et al., Can. J. Microbiol. 35:1141–1145 (1989).
Clark, G. F. et al., Arch. Biochem. Biophys. 257,1:217–229 (1987).
Doig, P. et al., Can. J. Microbiol. 32:160–166 (1986).
Pasloske, B. L. et al., J. Bacteriol. 170,8:3738–3741 (1988).
Paranchych, W. et al., Antibiot. Chemother. 36:49–57 (1985).
Watts, T. et al., Infect. and Immun. 42,1:113–121 (1983).
Beachey, E., J. Infect. Dis. 143,3:325–345 (1981).
Lee, K. K. et al., Infect. Immun. 57,2:520–526 (1989).

*Primary Examiner*—Christine M. Nucker
*Assistant Examiner*—Hazel F. Sidberry
*Attorney, Agent, or Firm*—Peter J. Dehlinger; Carol A. Stratford

[57] ABSTRACT

A peptide having a sequence corresponding to an antigenic site in the protein exoenzyme S which is antigenically similar to a C-terminal portion of the *Pseusdomonas aeruginosa* pilin protein is disclosed. The peptide is cross-reactive with surface peptides present in certain bacterial and fungal microorganisms, and is effective in inhibiting binding of such organisms to target epithelial cells. The peptide may also be employed in a vaccine composition, for producing immunity against such cross-reactive microorganisms.

2 Claims, 6 Drawing Sheets

```
                    Glu    Gln
                   (P,A) (M,K)    Phe
           Asp (E)
       Gln (V)                  (R,T) Ile
       Asp (T)                        Pro
       Ser (T)                  (N) Lys
       Thr (K,A)                     Gly
       Cys ——————— S ——————— S ——————— Cys
```

Fig. 1A

```
                         ↓
                    Ala       Thr
                  (E,P,A) (Q,M,K)
            — (D,E)              (F) Gly
            — (Q,V)              (I,R,T) —
        ⟶  Thr (D,T)              (P) Pro ⟵
        ⟶  Thr (S,T)              (K,N) Asn ⟵
        ⟶  Ala (T,K,A)            (G) Gly ⟵
                                  (-) Ser
        ⟶  Cys ——————— S ——————— S ——————— Cys ⟵
```

PSEUDOMONAS EXOENZYME S PEPTIDE COMPOSITION AND METHOD

1. Field of the Invention The present invention relates to Pseudomonas-derived polypeptide antigens, and to antibodies immunoreactive against the antigens.

2. References

Adams, M. H. Methods of study of bacterial viruses, p. 443-452. In M. H. Adams (ed.), Bacteriophages. Interscience Publishers, Inc., New York (1959).

Ausubel, F. M., et al., Current Protocols in Molecular Biology, John Wiley and Sons Inc., Media, Pa. (1990).

Baker, N. et al., Infect. Immun. 58:2361-2366. (1990).

Baker, N. Abstr. Annu. Meet. Am. Soc. Microbiol., B-224:68. (1989)

Beachy, E. H. 1981 J. Infect. Dis. 143:325-345 (1981).

Bryan, C. S. et al., Am. Rev. Respir. Dis. 129:668-671. (1984).

Carr, B., et al., Gerontology 35:127-129 (1989).

Coburn, J. et al., J. Biol. Chem. 264:9004-9008 (989).

Dale, R. K., B. A. McClure, and J. P. Houchins 1985. Plasmid 13:31-40.

Devereux, J., P. Haeberli, and O. Smithies 1984. Nucleic Acids Res. 2:387-395.

Devlin, J. J., et al., Science 249: 404 (1990).

Doig. P., et al., Infect. Immun. 56:1641-1646 (1988).

Doig, P., et al., Can. J. Microbiol. 35:1141-1145 (1989).

Doig, P., et al., Infect. Immun. 58:124-130 (1990).

Doig, P., et al., Infect. Immun. 56:1641-1646 (1988).

Farmer, J. J., III. Hosp. Pract. 10:63-70 (1976).

Franklin, A. L., et al., Infect. Immun. 55:1523-1525 (1987).

Geyson, H. M. et al., in Synthetic Peptides as Antigens; Ciba Foundation Symposium 119:131-149 (1986).

Godfrey, A. J. et al., Antimicrob. Agents Chemother. 30:802-805 (1986).

Hansson, G. C. et al., Biochem. Biophys. Acta 750:214-216 (1983).

Hazlett, L. D. et al., Infect. Immun. 51:687-689 (1986)

Irvin, R. T. and Ceri, H., Can. J. Microbiol. 31:268-275 (1985).

Irvin, R. T., et al., Microbial Ecology Health Disease, 3:39-47 (1990).

Irvin, R. T., et al., Infect. Immun. 57:3720-3726 (1989).

Komiyama, K. et al., Infect. Immun. 55:2364-2369 (19).

Krivan. H. C., et al., Arch. Biochem. Biophy. 260-49-3-496 (1988).

Krivan, H. C., et al., Proc. Natl. Acad. Sci. USA 85:6157-6161 (1988).

Kulczyki, L. L. et al., J. Am. Med. Assoc. 240:30-34 (1978).

Laraya-Causey, L. R. et al., J. Pediatr. 89:23-26 (976)

Lee, K. K., et al., Infect. Immun. 57:520-526 (1989).

Lee, K. K., et al, Inf Immunol, 58:2727-32 (1990).

Leprat, R. et al., Ann. Microbiol. (Paris) 131B:210-222 (1980).

Lund, B. et al., Proc. Natl. Acad. Sci. USA 84:5898-5902 (1987)

Marrs, C. F., et al., Am. J. Med. 88 (Suppl 5A): 36S-40S (1990).

McBride, L. J., et al., Clin Chem, 35:2196-2201 (1989).

McEachran, D. W., et al, Can. J. Microbiol. 31:563-569 (1985).

McEachran, D. W., et al., J. Microbiol. Meth. 5:99-111(1986).

Morrison, S. L., et al., Proc. Natl. Acad. Sci. USA 81:6851-6855 (1984).

Nieto, A., et al., Mol. Immunol. 21:537-543 (1984).

Paruchuri, D. K. et al., Proc. Natl. Acad. Sci. USA 98:333-337 (1990).

Pasloske, B. L., et al., J Bacteriol, 170:3738-3741 (1988).

Paranchych, W., et al., Can. J. Microbiol. 25:1175-1181.

Paranchych, W. et al., Advan. Microbiol. Phys. 29:53-114 (1988).

Rabbitts, T. H. et al., Nucleic Acids Res. 9:4509-4524 (1981).

Ramphal, R. et al., Infect. Immun. 55:600-603 (1987).

Sanger, F., S. Nicklen, and A. R. Coulson 1977. Proc Natl Acad Sci, USA 74:5463-5467.

Sato, H. and Okinaga, K., Infect. Immun. 55: 1774-1778 (1987).

Scott, J. K. and Smith, G. P., Science 249:386-390 (1990).

Sastry, L., et al., Proc. Natl. Acad. Sci. USA 86:5728-5732 (1989).

Sastry, P. A., et al., Can. J. Cell Biol. 63:284-291 (1985).

Singh, A. et al., Infect. Immun. 58:1301-13 (1990).

Sokol, P. A., Dennis, J. J., MacDougall, P. C., Sexton, M., and Woods, D. E. Microbial Pathogenesis 8:243-257 (1990).

Staddon, W., et al., Can. J. Microbiol. 36:336-340 (1990).

Stromberg, N. et al., J. Biol. Chem. 265:11252-11258 (1990).

Tabor, S., and C. C. Richardson 1987. Proc Natl Acad Sci, USA 84:4767-4771.

Todd, T., et al., Am. Rev. Respir. Dis. 140:1585-1589 (1989).

Towbin, M. et al., Proc. Natl. Acad. Sci. USA 76:4350-4354 (1979).

Tsai, C., et al., Anal. Biochem. 119:115-119 (1982).

Woods, D. E. et al., Infect. Immun. 29:1146-1151 (1980).

Woods, D. E. et al., Infect. Immun. 55:579-586 (1987).

Woods, D. E. et al., Eur. J. Clin. Microbiol. 4:163-169 (1985).

Woods, D. E. et al., In N. Hoiby, S. S. et al., (ed.) *Pseudomonas aeruginosa* Infection. Antibiot. Chemother. 42:27-35 (1989).

Worobec, E. A., et al., J. Biol. Chem. 260:938-943 (1985).

zu Putlitz, J., et al., Bio/Technology 8:651-654 (1990).

3. BACKGROUND OF THE INVENTION

During the past two decades, *Pseudomonas aeruginosa* has been recognized as a pathogen which causes between 10% and 20% of infections in most hospitals. Pseudomonas infection is especially prevalent among patients with burn wounds, cystic fibrosis, acute leukemia, organ transplants, and intravenous-drug addiction. *P. aeruginosa* is a common nosocomial contaminant, and epidemics have been traced to many items in the hospital environment. Patients who are hospitalized for extended periods are frequently affected by this organism and are at increased risk of developing infection. The most serious infections include malignant-external otitis, endophthalmitis, endoconditis, meningitis, pneumonia, and septicemia. The likelihood of recovery from Pseudomonas infection is related to the severity of the patient's underlying disease process. The reported mortality for P. aeruginosa pneumonia is as high as 50-80%. Even with the development of newer antibiotics, resistance remains a problem necessitating combined antibiotic treatment for severe P. aeruginosa infections.

Various therapies for the management of severe P. aeruginosa infections have been evaluated for many years, with particular attention focused on virulence factors. As with most bacterial pathogens, virulence of P. aeruginosa is multifactorial and is the product of many interacting variables, involving both the bacterium and the host. Evidence suggests that the initial event in infection is the adherence of microorganisms to epithelial cells of mucosal surfaces (Bleachy). Organisms that are unable to adhere to mucosal surfaces fail to colonize because they are removed by the secretions that bathe the mucosal surfaces (Bleachy). The adherence process is dependent upon the specific recognition between bacteria and epithelial cells, mediated through adhesin molecules present on the bacterial cell surface and receptors present on target cells.

Molecules which have been identified as adhesins in P. aeruginosa include alginate and pilus proteins. P. aeruginosa can utilize both pili and alginate (the principle component of the P. aeruginosa capsule) as adhesins to mediate attachment to human respiratory epithelial cells (Doig). Pili have been identified as an important adhesive factor for buccal cells (Woods 1980), damaged tracheal epithelium (Ramphal 1984), and mucous proteins (Ramphal 1987). In particular, a specific peptide domain of the pilus protein has been recognized as a determinant of the adhesive properties of these P. aeruginosa.

Gangliosides, and in particular, gangliotriosylceramide (GgO$_3$; GalNac$\beta$1-4Gal$\beta$1-4Glc$\beta$1-1Cer), gangliotetraosylceramide (GgO$_4$; Gal$\beta$1-3GalNAc$\beta$1-4Gal$\beta$1-4Glc$\beta$1-1Cer), and lactosylceramide (LacCer; Gal$\beta$1-4Glc$\beta$1-1Cer) have been identified as possible receptors for P. aeruginosa (Baker, Krivan), but the adhesin or adhesins responsible for this specificity have not been identified. P. aeruginosa can utilize both pili and alginate (the principle component of the P. aeruginosa capsule) as adhesins to mediate attachment to human respiratory epithelial cells (Doig). However, strains exist which lack both pili, and ability to synthesize alginate and which still retain the capacity to attach to epithelial cells, thereby suggesting the existence of additional adhesin molecules.

Earlier filed co-pending and co-owned U.S. patent applications (Ser. Nos. 638,492 and 344,565) disclose P. aeruginosa peptides derived from the C-terminal region of the P. aeruginosa pilin protein, and specifically, the C-terminal region which includes two Cys residues and the intervening amino acid residues. The derived region of representative peptides vary in length between 14 and 19 amino acid residues, including the two Cys residues, and are prepared in both oxidized (disulfide-linked) and reduced (non-cyclized) form. The peptides (in both reduced and oxidized form) were shown to have the following properties:

(a) ability to bind to human tracheal epithelial cells (TECs) and human buccal epithelial cells (BECs);

(b) ability to inhibit binding of Pseudomonas pilin peptide to tracheal epithelial cells (TECs) and buccal epithelial cells (BECs);

(c) ability to elicit serum antibodies which are immunoreactive with Pseudomonas pilin peptide;

(d) ability to elicit serum antibodies which block binding to Pseudomonas pilin peptide to BECs; and (e) ability to inhibit binding of unrelated bacterial and fungal organisms to human BECs and/or tracheal epithelial cells (TECs).

It was further shown, in studies conducted in support of these applications, that monoclonal antibodies prepared against the Pseudomonas-derived peptide were effective in blocking fungal cell adherence to BECs.

It has now been discovered that exoenzyme S (Exo S), a bacterial toxin having ADP ribosyl transferase activity which is present on the surface of P. aeruginosa cells, also binds to BECs with a specificity which is similar to that exhibited by bacterial cells. Antibodies which are directed against the pilus peptide domain earlier recognized as a determinant of bacterial binding cross react with purified Exo S. The binding region includes a segment of the amino acid sequence of Exo S having about 60-70% sequence homology with the above pilus peptide domain found to be a determinant of bacterial binding to target cells.

These combined findings show that the Exo S-derived peptide, and antibodies produced in response to the peptides, are capable of inhibiting infections in which the infecting microorganism has surface proteins which are immunologically crossreactive with antibodies produced against the peptide region of Exo S protein.

4. SUMMARY OF THE INVENTION

The invention includes, in one aspect, a peptide containing an epitope formed by the sequence identified as SEQ ID No: 2.

The peptide of the invention is further characterized by (a) immunospecific binding to monoclonal antibody PK99H or MCA1; (b) a peptide length less than 20 amino acid residues; and (c) ability to block binding of Pseudomonas aeruginosa to buccal epithelial cells.

In another aspect, the peptide of the invention includes the sequence identified SEQ ID No: 2.

In a related aspect, the invention includes a method of producing immunity against infection by Pseudomonas aeruginosa. In this method, a peptide containing an epitope formed by the sequence identified as SEQ ID No: 2 is administered to a patient in a pharmaceutically expedient excipient. The peptide used in the vaccine is further characterized by (a) immunospecific binding to monoclonal antibody PK99H or MCA1; (b) a peptide length less than 20 amino acid residues; and (d) ability to block binding of Pseudomonas aeruginosa to buccal epithelial cells.

In a preferred embodiment, peptide used in the method of the invention has an immunogenic epitope contained in the sequence identified as SEQ ID No: 2, where the two cysteine residues (C) are linked covalently, In this embodiment, the peptide is further recognized by monoclonal antibody MCA.

In yet another embodiment, the peptide used in the method of the invention includes the sequence identified as SEQ ID No: 2, where the two cysteine (C) residues are linked covalently.

Alternatively, the method of the invention may employ a peptide having an epitope which includes the sequence identified as SEQ ID No: 2.

These and other objects and features of the present invention will be come more fully apparent when the following detailed description of the invention is read in conjunction with the accompanying drawings.

DETAILED DESCRIPTION OF THE INVENTION

I. Definitions

The terms "epitope" and "epitopic," as used herein, designate the structural component of a molecule that is responsible for specific interaction with corresponding antibody (immunoglobulin) molecules elicited by the same or related antigen.

The term "antigen," as used herein, means an entity that is recognized by an antibody.

The term "immunogen," as used herein, describes an entity that induces antibody production in the host animal. In some instances the antigen and the immunogen are the same entity, while in other instances the two entities are different.

The term "immunologically mimics" is used herein to mean that an immunogenic polypeptide of this invention is not a natural protein or a cleaved fragment of a natural protein, but a manufactured polypeptide, as by solid phase synthesis or genetic engineering techniques, which polypeptide induces production of antibodies that bind to the inducing polypeptide and also to a corresponding pilin or pilin polypeptide portion.

All amino acid residues identified herein are in the natural or L-configuration unless otherwise specified. In keeping with standard peptide nomenclature, abbreviations for amino acid residues that have been used herein are as follows:

| Symbol | | |
|---|---|---|
| 1 Letter | 3 Letter | Amino Acid |
| Y | TYR | L-tyrosine |
| G | GLY | glycine |
| F | PHE | L-phenylalanine |
| M | MET | L-methionine |
| A | ALA | L-alanine |
| S | SER | L-serine |
| I | ILE | L-isoleucine |
| L | LEU | L-leucine |
| T | THR | L-threonine |
| V | VAL | L-valine |
| P | PRO | L-proline |
| K | LYS | L-lysine |
| N | ASN | L-asparagine |
| H | HIS | L-histidine |
| Q | GLN | L-glutamine |
| E | GLU | L-glutamic acid |
| W | TRP | L-tryptophan |
| R | ARG | L-arginine |
| D | ASP | L-aspartic acid |
| C | CYS | L-cysteine |

The terms "glycosphingolipids," "GSL" and "gangliosides" are used interchangeably to describe a sphingolipid consisting of a ceramide having an attached oligosaccharide chain containing at least one acidic sugar. A common acidic sugar is N-acetylneuraminate, which is also known as "sialic acid." Asialo GM1 refers to the ganglioside GM1 from which the sialic acid has been removed, which is also technically termed "cerebroside." Abbreviations used to describe the sugar substitutions found in gangliosides and in polysaccharides include Gal, galactose; Glc, glucose; GalNac, N-acetylgalactosamine; NAN, N-acetylneuraminate.

II. Exo S

Exo S (ExoS) is a toxin which has been shown to be present on the outer surface of P. aeruginosa cells. The enzyme has catalytic (ADP ribosylation) as well as cytotoxic properties which are separable, as described in section IV below. Purification and cloning of this enzyme toxin have been achieved (Woods 1987, 1990), and the partial DNA sequence of the HinSaI fragment of the cloned gene has been used to identify a region having relative sequence homology to known adhesin domains residing in the pilin proteins of P. aeruginosa. The DNA and predicted amino acid sequence of the homologous segment of ExoS are presented as SEQ ID No: 1 and SED ID No: 2, respectively.

The amino acids in bold represent amino acids homologous to those found in pilin (KB7). The significance of this homology is that the amino acid sequence in pili bounded by the cysteine residues has been shown to be the epithelial binding domain of pili. As will shown below, Exo S is also an adhesin which binds to the same receptors as do pilin proteins and peptide fragments.

Figure 3:
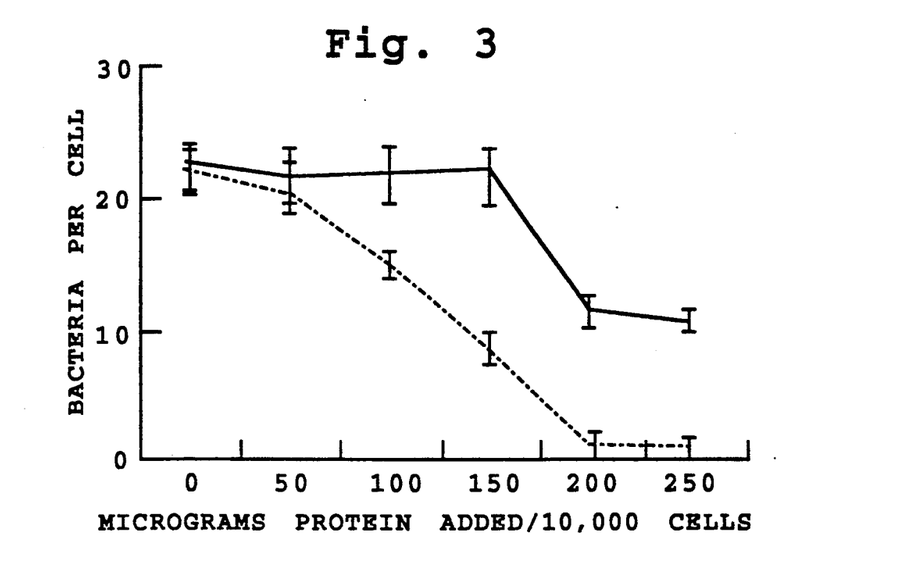
FIG. 3 is a plot showing the effect of purified Exo S (dotted line) or purified pili (solid line) to block adherence of intact P. aeruginosa strain DG1 to buccal epithelial cells.

Purified ExoS was additionally utilized in experiments comparing its ability with that of purified pili to compete with intact Pseudomonas cells for adherence to buccal epithelial cells (BECs). Experimental protocols for these experiments are described in Example 5. FIG. 3 shows the results of experiments in which Exo S and purified PAK pili were compared for ability to compete for binding of intact P. aeruginosa strain DG1 to BECs. Incubation of buccal cells with purified Exo S inhibited the binding of bacteria to the cells in a concentration-dependent manner (FIG. 3, dashed line). When present at a concentration of 200 μg of protein/10,000 cells Exo S inhibited virtually all binding of bacterial cells to BECs, whereas the same concentration of purified pili reduced adherence only by approximately 50% (FIG. 3, solid line).

III. P. aeruginosa Pilin and Exo S Peptides

Figure 1A:
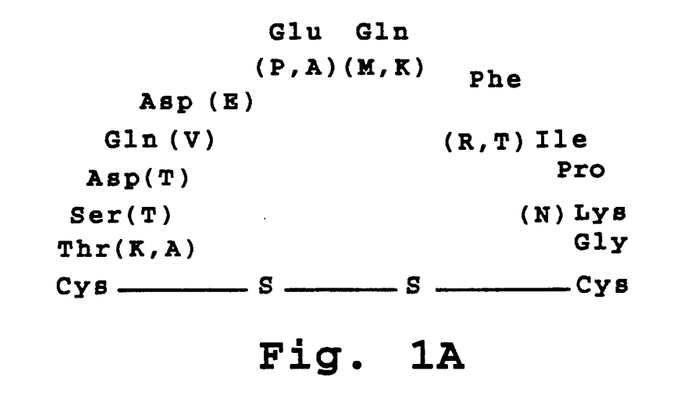
FIGS. 1A and 1B show sequences of a Pseudomonas pilin-derived peptide having epithelial cell adhesion inhibitory properties (1A) and the Exo S-derived peptide of the invention (1B)

FIG. 1A shows the amino acid sequence of residues 131-143 of the pilin protein from *P. aeruginosa* strain PAK in three-letter amino acid code. Shown in parentheses in one-letter amino acid code are substitutions to this sequence which are a composite of internally consistent amino acid variations of the homologous regions of the pilin proteins derived from five strains of *P. aeruginosa* (PAK, PAO, CD4, K122, and KB7). These sequences and the composite peptide were reported in earlier co-pending U.S. patent application, Ser. No. 638,492, which is incorporated herein by reference. In that application, it was noted that the internal-variation substitutions are those substitutions found in nature, and are therefore apparently compatible with requisite antigenic properties of the peptide. Thus, for example, in the composite pilin peptide of FIG. 1A, the residue immediately C-terminal to the N-terminal Cys could alternatively be Threonine, Lysine or Alanine.

The sequences shown in FIG. 1A form a portion of peptide comprising residues 131-143 of the pilin protein. Peptides having sequences characterized by the composite peptide of the invention, comprising residues 128-144 of the pilin protein were shown to be useful in inhibiting adhesion of *P. aeruginosa* and related organisms to epithelial cell targets, and in producing vaccines suitable for protecting an organism from infections caused by such organisms.

Figure 1B:
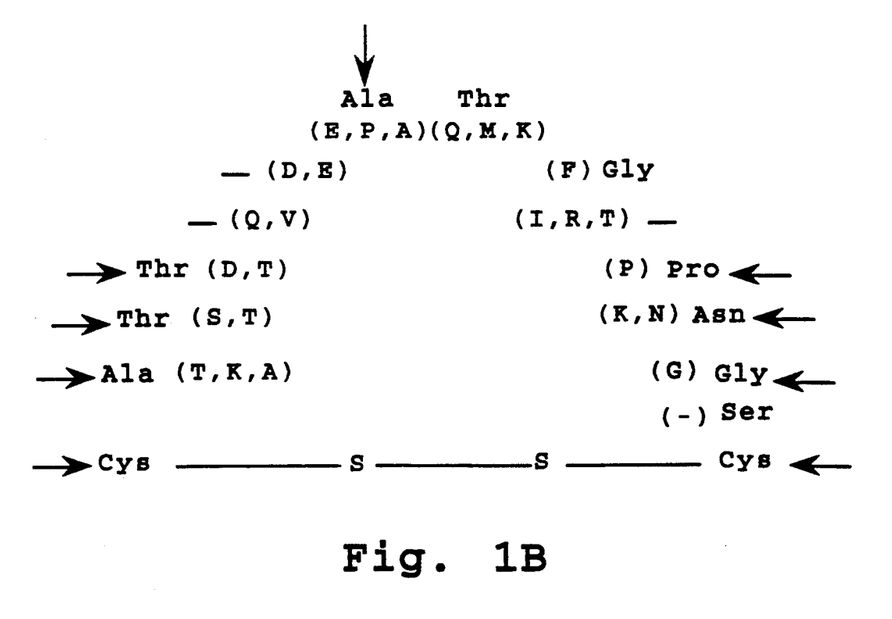

Partial sequencing of a DNA clone of purified Exo S, described in Examples 1 and 2, has revealed a sequence, shown in FIG. 1B in three-letter amino acid code, which is partly homologous to the pilin peptide region 131-143, described above. This peptide, and more particularly, the epitope formed by the sequence of this peptide, is referred to as exo S peptide. Also shown in FIG. 1B, for purposes of comparison, are the amino acid substitutions (shown in one letter code) of the analogous region of the pilin peptide described above.

As described further below, it has been now been discovered that ExoS displays cross immunoreactivity with antibodies which are directed to the Pseudomonas-derived pilin peptides described above. Such antibodies, and in particular, one known as monoclonal antibody PK99H (Mab PK99H), which was described in the co-pending U.S. patent application Ser. No. 638,492 described above, have the ability to block binding of *P. aeruginosa* and its pili to target epithelial cells. Furthermore, certain antibodies directed against Exo S are cross-reactive with *P. aeruginosa* pili and can inhibit binding of *P. aeruginosa* to epithelial cells.

According to one aspect of the invention, exo S peptide shares with pilin peptides the ability to (a) react with monoclonal antibody PK99H and (b) block binding of *P. aeruginosa* and microorganisms sharing reactivity with mAb PK99H to epithelial cells. In addition, the exo S peptide of the invention can be bound by a monoclonal antibody identified as Mab MCA1, with consequent inhibition of the of binding to epithelial cells.

The PK99H Mab was prepared against the PAK pilin protein containing peptide residues 128-144 (in oxidized form) and has been shown to be cross-reactive with various other *P. aeruginosa* strain pili. The requirement that the peptide of the invention have crossreactivity with this antibody ensures that the peptide has requisite epitopic similarity to the pilin peptides shown to block adhesion of *P. aeruginosa* to epithelial cells.

As will be described below, the epitopic region of the peptide of the invention has the ability to bind to a receptor site on human buccal epithelial cells (BECs), and this binding is effective to inhibit *P. aeruginosa* binding to these epithelial cells. The requirement for peptide epitope binding to these cells ensures that the peptide has the requisite receptor binding activity.

The peptides of the invention can be synthesized by conventional solid phase synthetic methods, as described in Example 3. Alternatively, peptides of the invention may be produced by recombinant means, using the cloning vectors and sequences described in Example 2. The peptides of the invention may contain additional N-terminal or C-terminal residues, consistent with the above constraints.

IV. Anti-Exo S antibodies

This section summarizes methods of production, and antibody binding characteristics of polyclonal and monoclonal antibodies which are immunoreactive with the peptides of the invention. The antibodies are useful producing passive immunity in an organism to pathogens which have adhesin molecules characterized by epitopes formed by exo S peptide.

IVA. Polyclonal Antibodies

Polyclonal antibodies specific against reduced and oxidized forms of PAK peptide were prepared as described in the earlier-filed co-pending application, and as published (Lee). Briefly, PAK peptides were conjugated to keyhole limpet hemocyanin (KLH), and the conjugate was used to immunize female Flemish rabbits. The peptides include the PAK peptide in reduced ($PAK_{red}$) and oxidized form ($PAK_{ox}$) form. Rabbits were given an initial immunization, two weeks later given a booster immunization, and then bled two weeks later. An immunoglobulin fraction was purified by Protein A affinity chromatography. Antibody binding to native PAK pilin protein, PAK peptide, and PAO peptide was examined by standard ELISA procedures (Worobec). Antibody specificities were as follows:

(a) The antisera produced by both $PAK_{ox}$ and $PAK_{red}$ was able to bind native PAK pili, and the titres raised against both peptides were similar;

(b) The antisera raised against the $PAK_{ox}$ peptide was strongly crossreactive with native PAO pili; and (c) The antisera raised against the $PAK_{red}$ peptide was only weakly crossreactive with native PAO pili.

The results show that, although both oxidized and reduced forms of the peptide are effective to induce antibodies which are reactive with same-species pilin protein, the oxidized (disulfide-linked) form of the peptide is important for stimulating production of antibodies which are cross-reactive with pilin proteins from other *P. aeruginosa* strains.

Polyclonal antibodies to purified Exo S (polyclonal anti Exo S) were prepared as published by Woods (1987), using New Zealand rabbits. In some cases, antisera were adsorbed with *P. aeruginosa* strain DG-ExS5, deficient in production of Exo S (Woods 1985), prior to use.

Figure 2A:
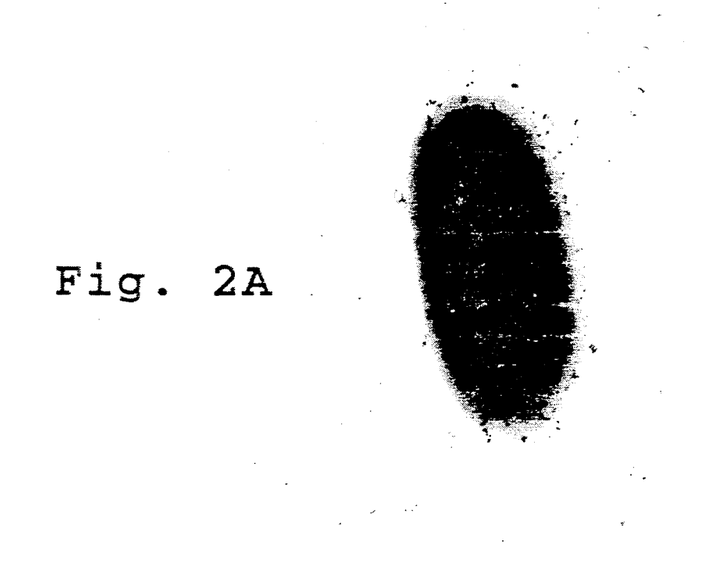
FIGS. 2A and 2B show immunoelectron microscopy of P. aeruginosa cells exposed to monoclonal antibody raised against purified Exo S (2A) or phosphate buffered saline (2B) followed by protein A-colloidal gold.
Figure 2B:
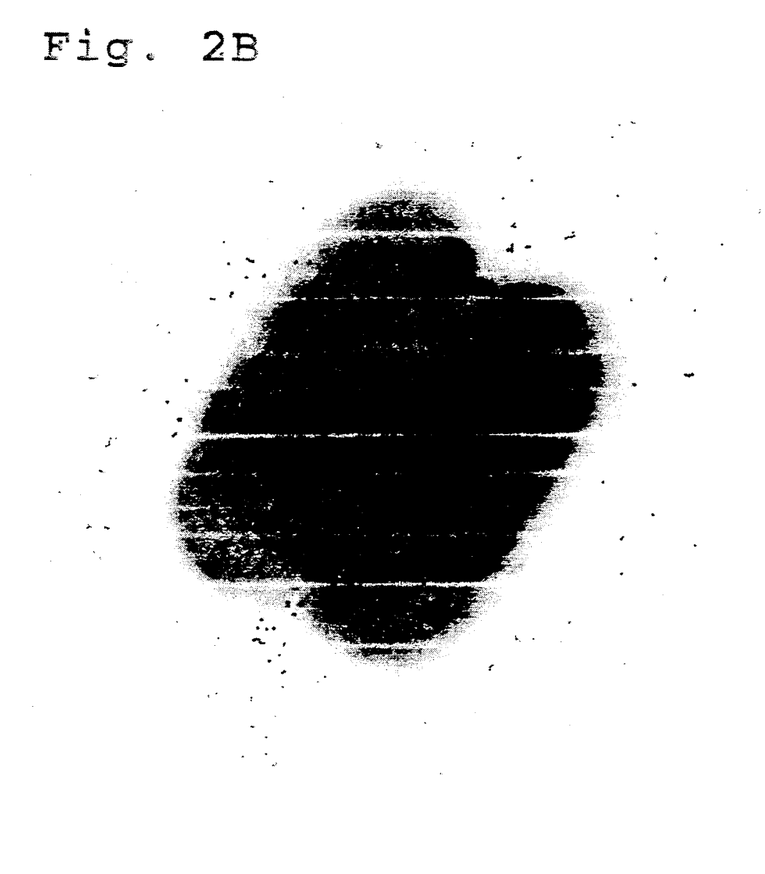

The presence of Exo S on the surface of *P. aeruginosa* was confirmed by the immunolabeling experiments illustrated in FIGS. 2A and 2B. In these experiments, bacterial cells were exposed to polyclonal anti-exo S (2a) or saline carrier, prior to exposure to colloidal gold conjugated to protein A or anti-rabbit IgG. Gold beads were observed as a uniform coating on the cell surfaces of those cell preparations exposed to anti-exo S (FIG. 2A). In contrast, control cells incubated in the absence of antibody to Exo S did not reveal any beads on the cell surfaces (FIG. 2B).

Polyclonal antibodies to Exo S were additionally utilized in experiments examining their cross-reactivity with pili derived from *Pseudomonas aeruginosa* strains PAK, PAO, and P1 and with pilin peptide PAK $(128-144)_{ox}$ described in detail below (Table 2) and in Example 6. Polyclonal antibodies to PAK, and to PAK pilin peptide PAK$(128-144)_{ox}$ were also tested for cross reactivity with various pili, and with Exo S.

IIIB. Monoclonal Antibodies

Monoclonal antibodies against native PAK pili protein were prepared according to methods described elsewhere by the inventors (Doig). Briefly, BALB/c mice were immunized with weekly injections of PAK pili. Spleen cells from the animals were fused with mouse myeloma cell line NS1 (Irvin), and successful fusions were screened by an ELISA method for ability to secrete anti-pilin antibody. A library of 262 hybridoma clones that secreted antibodies immunoreactive with PAK pili were obtained. Protein A purified monoclonal antibodies were then screened against pilin peptide fragments (Doig), to determine specificities of these antibodies. Four hybridoma cell lines were selected for further specificity studies: cell lines PK99H, PH34C, PK3B, and PK41C.

Immunoblots of purified PAK and PAO pili revealed that PK99H and PK3B Mabs were specific for PAK pilin protein, while PK34C and PK41C Mabs were immunoreactive with both PAK and PAO pilin peptide. PK99H and PK34C Mabs were both immunoreactive with a C-terminal fragment of PAK pilin.

In copending U.S. patent application Ser. No. 638,492, Fab fragments prepared from PK99H and PK34C were shown to inhibit Pseudomonas pili binding to BECs, indicating their specificities for the adhesin domain of the pilin protein.

Monoclonal antibodies to purified Exo S were prepared as published elsewhere by one of the inventors (Woods 1987) and detailed in Example 4B. Briefly, antigen for injection was prepared from a purified preparation of Exo S which was subjected to dialysis against 1% formalin in 0.1M Tris buffer (pH 8.0) and 0.2M L-lysine, followed by dialysis against 0.2M L-lysine in 0.85% NaCl, pH 6.3 prior to injection into BALB/c mice. Dispersed spleen cells from the mice were fused with NS-1 cells using 50% (wt/wt) polyethylene glycol (MW 1500). Supernatants of fused cells in culture were tested for production of antibody to Exo S, using an ELISA procedure. Positive cell lines were subcloned extensively and were injected into pristane primed mice for ascitic tumor production. Antibodies present in ascitic fluid were purified and immunoreactivity was verified using purified Exo S in Western blots.

Monoclonal antibodies to Exo S were additionally tested for ability to a) inhibit enzyme (ADP ribosylation) activity and b) neutralize cytotoxic effects of Exo S, as described by Woods (1987). Monoclonal antibody MCA1 was able to neutralize cytotoxic activity, but has relatively low potency in inhibition enzyme activity. Monoclonal antibody MCA2 was found to have much greater potency in inhibition of enzyme activity, but relatively low potency in neutralizing the cytotoxic effects of Exo S. MCA2 was subsequently used in purification of the protein (Woods, 1987). Monoclonal antibody MCA3 was shown to inhibit enzyme activity, but not neutralize cytotoxicity.

In experiments testing the ability of these monoclonal antibodies to interfere with binding of *P. aeruginosa* to BECs, it was found monoclonal antibody MCA1, which neutralizes the cytotoxicity of Exo S, but has no effect on enzymatic activity, reduced adherence of bacteria to background levels (Table 1). Monoclonal antibody MCA3, which neutralizes enzymatic activity but not cytotoxicity, did not inhibit the adherence of Exo S to buccal cells.

TABLE 1

Effect of Monoclonal Antibodies to Purified Exo S on *Pseudomonas aeruginosa* Adherence to Buccal Epithelial Cells.

| Monoclonal Antibody[1] | Strain | Adherence[2] |
|---|---|---|
| None-control | PAO | 22.1 ± 2.5 |
| None-control | DG1 | 26.7 ± 3.4 |
| MCA1[3] | PAO | 1.7 ± 0.3[4] |
| MAC1 | DG1 | 0.8 ± 0.1[4] |
| MCA3[5] | PAO | 21.9 ± 3.6 |
| MCA3 | DG1 | 25.8 ± 4.2 |

[1]Monoclonal antibodies prepared as previously described (27).
[2]Adherence assay performed as described (26). Values represent mean ± S.D.
[3]Neutralizes cytotoxicity but not enzymatic activity.
[4]Significantly different from control (p > 0.01).
[5]Neutralizes enzymatic activity but not cytotoxicity.

V. Immunocrossreactivity of Antibodies to Exo S and Pilin Proteins

Direct ELISA experiments were performed to examine immunocrossreactivity between antibodies to pilin proteins and to Exo S and their respective antigens. Table 2 shows the results of experiments in which the antigens listed in column 2 of the table were coated on microtiter plates. After appropriate blocking and washing of the plates, as described in Example 6A, serial dilutions of the antibodies listed in column 1 of the table were added to and incubated in the coated wells. The presence of bound antibody was detected by addition of an appropriate enzyme-conjugated species-appropriate second antibody and enzyme substrate capable of producing a color reaction. Titers with respect to the antigen tested were determined by noting the highest serial dilution of antibody at which a significant color reaction was detected. Thus, in the case of PAK pili antigen, a reaction was detected with Mab PK99H at greater than $10^6$ fold dilution of the stock antibody solution. In contrast, using PAK pili as antigen, polyclonal antiserum to Exo S (anti-exo S) yielded a detectable signal at $4 \times 10^4$ fold dilution of serum. This titer may be referenced to the titer of anti-exo S determined ($3.2 \times 10^6$) when Exo S itself was used as antigen. From the table the following interactions are apparent: (1) Mab PK99H recognizes PAK pili > exo S > P1 pili, and does not recognize PAO pili. (2) Polyclonal antibody to PAK pili recognizes PAK pili = Exo S and does not appreciably recognize PAO pili or P1 pili; (3) Polyclonal antibody to pilin peptide (128–144)ox derived from PAK pili recognizes PAK peptide (128–144)ox > PAK pili > Exo S > P1 pili; and (4) Polyclonal antibody to Exo S recognizes Exo S > PAK (128–144)ox = PAK pili = PAO pili > P1 pili. It is apparent from this analysis that the Exo S antibody is generally reactive with pilin-associated adhesin components of Pseudomonas.

TABLE 2

Cross-Reactivity with *Pseudomonas aeruginosa* Pili and Exo S
Direct ELISA Data:

| Antibody | Antigen: PAK pili Titre |
|---|---|
| PK99H | $>>10^6$ |
| Polyclonal anti-PAK | $>>10^6$ |
| Polyclonal anti-exo S | $4 \times 10^4$ |
| Polyclonal anti-PAK(128-144)$_{ox}$ | $>>10^6$ |

| Antibody | Antigen: PAO pili Titre |
|---|---|
| PK99H | NE |
| Polyclonal anti-PAK | NE |
| Polyclonal anti-exo S | $4 \times 10^4$ |
| Polyclonal anti-PAK(128-144)$_{ox}$ | X |

| Antibody | Antigen: P1 pili Titre |
|---|---|
| PK99H | $1.1 \times 10^4$ |
| Polyclonal anti-PAK | NE |
| Polyclonal anti-exo S | $1.1 \times 10^4$ |
| Polyclonal anti-PAK(128-144)$_{ox}$ | $1.1 \times 10^4$ |

| Antibody | Antigen: Exo S Titre |
|---|---|
| PK99H | $1.6 \times 10^5$ |
| Polyclonal anti-PAK | $>>10^6$ |
| Polyclonal anti-exo S | $3.2 \times 10^6$ |
| Polyclonal anti-PAK(128-144)$_{ox}$ | $3.2 \times 10^6$ |

| Antibody | Antigen: BSA-PAK(128-144)$_{ox}$ Titre |
|---|---|
| PK99H | ND |
| Polyclonal anti-PAK | ND |
| Polyclonal anti-exo S | $4 \times 10^4$ |
| Polyclonal anti-PAK(128-144)$_{ox}$ | $6.4 \times 10^7$ |

Competitive ELISA assays were carried out to further examine the ability of anti-Exo S antibodies to distinguish between heterologous binding sites. Methods used in this analysis are described in Example 6B. Briefly, microtiter plate wells were coated with purified PAK or PAO pili, blocked and washed to remove unbound materials. Test competitor was then mixed and pre-incubated with a concentration of anti-exo S polyclonal antibody sufficient to produce less than or equal to 50% of maximal binding signal, when anti-exo S antibody was added in the absence of competitor. The test mixture was then added to wells of o the microtiter plate.

Figure 4A:
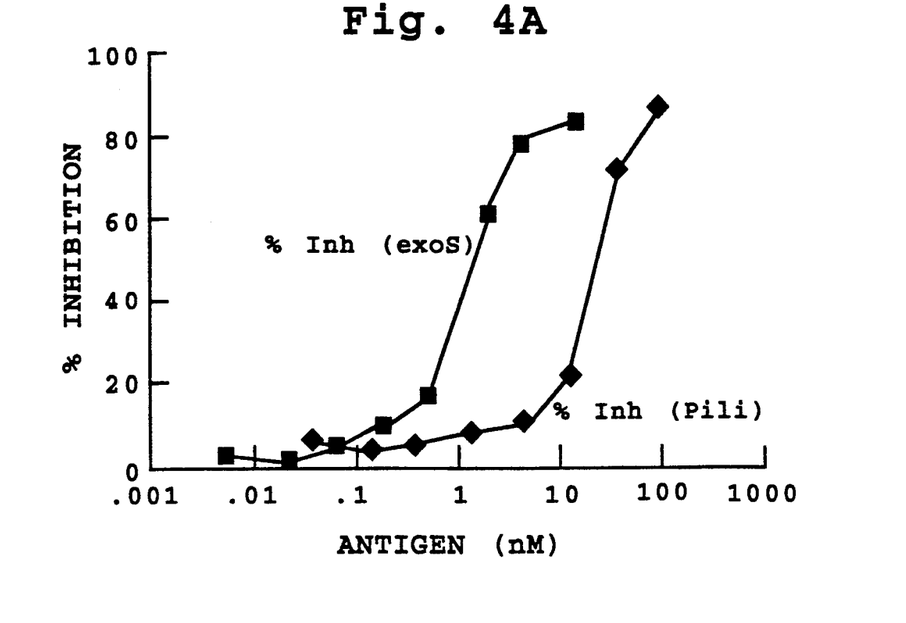
FIGS. 4A and 4B show the results of competitive ELISA experiments comparing abilities of PAK pili (4A) or PAO pili (4B) to Exo S to compete for binding of polyclonal anti-Exo S to PAK pili.

FIG. 4A shows the results of experiments in which PAK pili were used as plate coating and test competitor. As seen, Exo S was more potent than were PAK pili in interfering with binding between anti-exo S antibody and PAK pili. In contrast, it can be seen in FIG. 4B that Exo S and PAO pili were essentially equipotent in interfering with binding of anti-exo S antibody to PAO pili coated in the wells.

VI. Identification of Adhesin Receptor Molecules

This section describes studies in which specific adhesin molecules were tested for their abilities to specifically bind to and discriminate between glycosphingolipids.

Binding of *P. aeruginosa* and Exo S to GSLs. Methods for examining the binding of *P. aeruginosa* strain DG1 and Exo S derived from *P. aeruginosa* strain DG1 to GSLs on TLC plates, are described in Example 7A. Identities and locations of the GSLs to which bacteria or enzyme bind were determined by comparing sites of positive binding of antigen. Binding of both the intact bacterial cells and the isolated enzyme to GgO4 (gangliotetraosylceramide; Gal$\beta$1-3GalNAc$\beta$1-4Gal$\beta$1-4Glc$\beta$1-1Cer) (asialoGM$_1$) and LacCer (lactosylceramide; Gal$\beta$1-4Glc$\beta$1-1Cer) was clearly evident from the studies, as was binding to the trihexosylceramide region of the dog mucosa sample. Binding to GgO3 (gangliotriosylceramide; GalNac$\beta$1-4Gal$\beta$1-4Glc$\beta$1-1Cer; asialo-GM1) was also detected (not shown). No bands were detected if the overlay with Exo S was omitted from the assay. This binding specificity is in agreement with previously published reports for many strains of *P. aeruginosa* (Baker 1990, Krivan 1988). Neither Exo S nor strain DG1 bound to the sialylated GSLs, GM$_1$, or GM$_2$.

Binding of ExoS to GSL's is described in Example 7B (1). Binding curves of Exo S to dilutions of GSLs immobilized on plastic plates shown in FIG. 5 revealed optimum binding at approximately 1 $\mu$g of GgO4 (ASGM-1, asialoGM1). The reduced binding at 10 $\mu$g GgO4 is most likely an artifact of the assay related to the coating of the plate at high concentrations of GSL, since this phenomenon is also observed with whole bacteria (not shown).

Figure 6A:
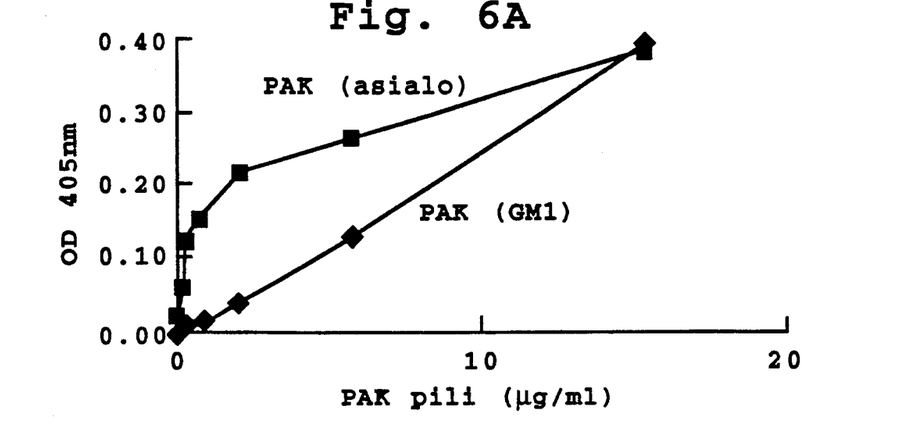
FIGS. 6A, 6B and 6C shows a plot of binding of PAK pili (6A), PAO pili (6B), and purified Exo S (6C) to glycosphingolipids mono- and asialo-GM1.
Figure 6B:
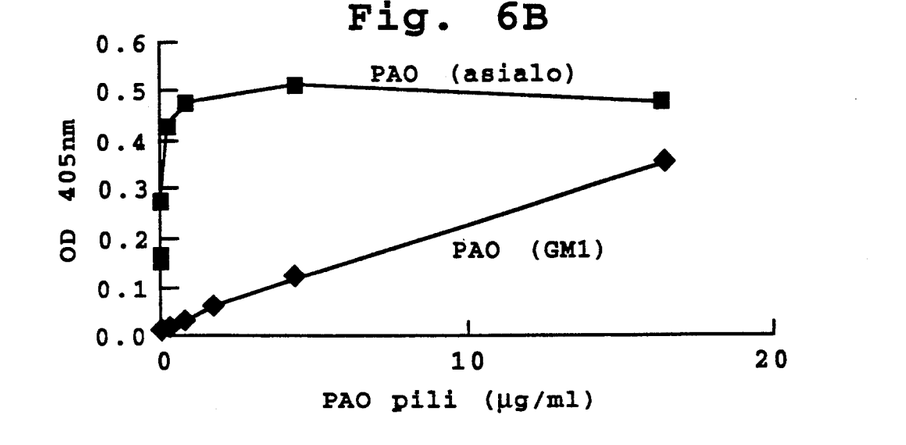
Figure 6C:
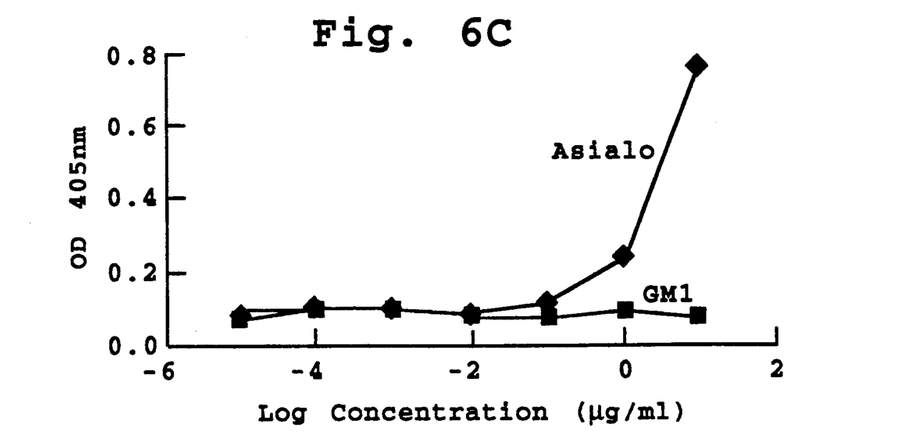
Figure 7:
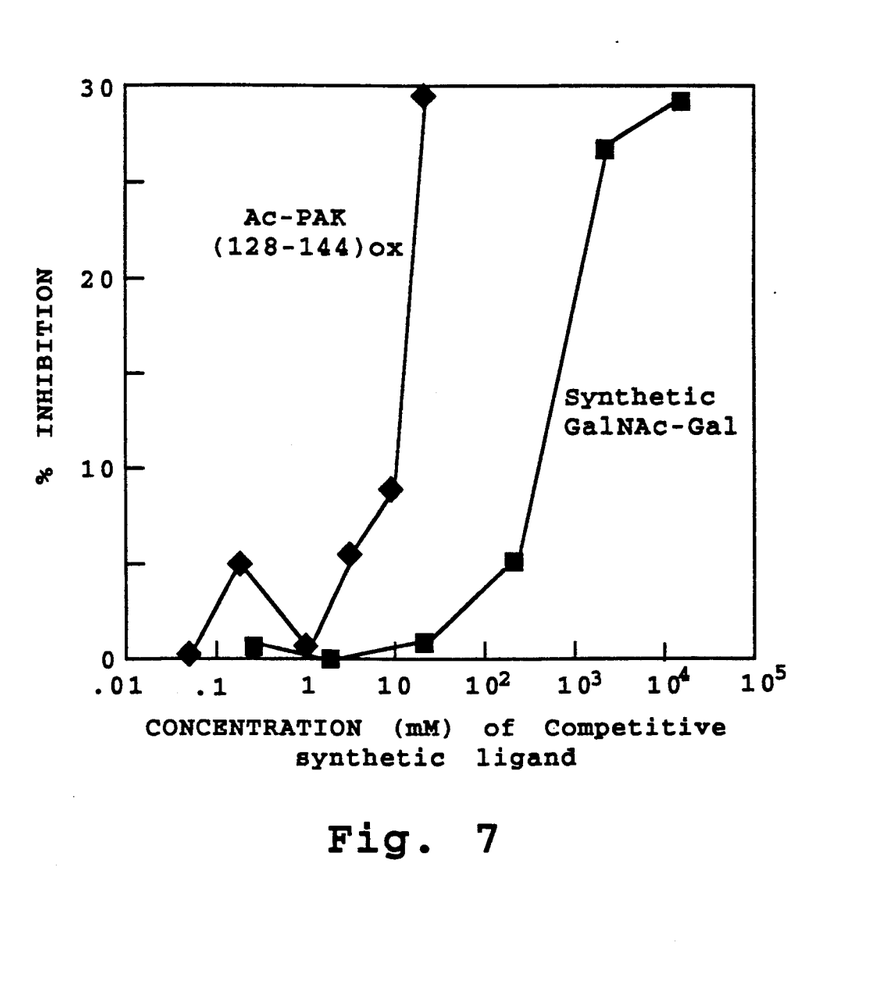
FIG. 7 shows a plot of the inhibition of binding of PAK pili to GalNAcGal-BSA by peptide Ac-PAK(128-144)ox (solid diamonds) and by GalNac-Gal (open squares).

Binding of pili to GSLs. A solid phase GSL binding assay described in Example 7B was used to assess binding of purified pili to mono- and asialo-GM1. In this assay, GSLs were adsorbed to the wells of 96-well microtiter plates, washed and exposed to test agent. Presence of bound agent was detected by subsequent addition of an appropriate agent-specific antibody, followed by enzyme conjugated second antibody. Binding of PAK pili, PAO pili, and for comparison, Exo S to asialo GM1 and monosialo GM1 is shown in the binding curves represented in FIGS. 6A, 6B, and 6C, respectively. In the plots shown in FIGS. 6A and 6B, binding to monosialo GM1 is represented by solid diamonds, and binding to asialo-GM1 is represented by open squares. In the plots shown in FIG. 6C, binding to monosialo GM1 is represented by open squares, and binding to asialo-GM1 is represented by closed triangles. Apparent K$_m$'s of binding to each of these species were calculated from reciprocal plots of the binding data. A summary of the K$_m$ values (which represent the approximate concentration of ligand required to saturate 50% of the receptor sites under the experimental conditions) is given in Table 4.

TABLE 4

K$_m$ values for binding to Asialo- and mono-sialo-GM1

| | Apparent K$_m$ of Binding to | |
|---|---|---|
| | Asialo-GM1 | Mono-sialo-GM1 |
| PAK pili | 0.14 $\mu$g/ml | ND[1] |
| PAO pili | $1.7 \times 10^{-2}$ $\mu$g/ml | 15.65 $\mu$g/ml |
| Exo S | 1.29 $\mu$g/ml | ND |

[1]The affinity of PAK pili and Exo S for mono-sialo-GM1 was too low for a determination of the apparent K$_m$ of binding due to the low signal.

Binding of pili to oligosaccharides

Binding of purified pili to the sugar moieties representative of those present in reactive gangliosides was achieved by first conjugating the sugar moiety to bovine serum albumin (BSA), then adsorbing the BSA-conjugated sugar moiety to the wells of microtiter plates. FIG. 9 shows results of experiments wherein binding of PAK pili to immobilized $\beta$GalNAc1-4$\beta$Gal-BSA was carried out in the presence of increasing concentrations of competitors PAK pilin derived peptide Ac-PAK(128-144)ox, comprising the 17 amino acid sequence of PAK pilin protein residues 128 –144 *having acetylated * (solid diamonds), and free disaccharide GalNAc-Gal. The ability of the synthetic peptide region of the pilin protein to effectively compete for binding to the substrate indicates that recognition of the immobilized disaccharide was effected at least in part by this region of the protein.

VII. Inhibiting Bacterial Infections

As demonstrated above, antibodies produced against Exo S and particularly those showing activity in inhibiting the cytotoxic effects of Exo S, such as monoclonal antibody MCA1, are effective to inhibit adhesion of intact Pseudomonas cells to buccal epithelial cells. Antibodies produced against Exo S have been shown to be immunoreactive with pilin protein from a variety of P. aeruginosa strains (Table 2).

The invention thus includes, in another aspect, a method of blocking attachment to target epithelial cells, of organisms which have surface proteins which are antigenically crossreactive with antibodies produced against the bacterial toxin Exo S. The method includes contacting the microorganism with such antibodies produced against Exo S to bind to the crossreactive surface protein. This binding is then effective to block binding of the microorganism with target epithelial cells, such as BECs.

The peptide used to produce the antibody is preferably selected from peptides containing epitopes formed by the sequence identified as SEQ ID No: 2 and having the characteristic of immunospecific binding to monoclonal antibody MCA1, as discussed in Sections II and IV.

Alternatively, the peptide used to produce the antibody is one selected for its cross-reactivity with bodies produced to P. aeruginosa pilin, and particularly those antibodies, such as PK99H, directed to the C-terminal pilin peptide characterized as containing the binding epitope which recognizes target epithelial cells as described in Section III.

The antibody, either polyclonal or monoclonal, may be generated by standard methods, such as those outlined in Section IIIB. One antibody useful in the method is the MCA1 monoclonal antibody described in Section IIIA. For therapeutic purposes, i.e., where the antibody is administered parenterally, the antibody is preferably a chimeric antibody containing the variable region of a mouse monoclonal antibody, such as antibody MCA1, and the constant region of a human immunoglobulin gene. Details of preparing such an chimeric antibody of this type are known in the art. Alternatively, the antibody may be produced by vaccination with a peptide containing the immunogenic region formed by the Exo S peptide sequence identified as SEQ ID No: 2, as described in Section VIII.

Microorganisms which are responsive to such treatment can be readily identified by the methods described above, for example, by showing binding of antibodies prepared against Exo S peptide to the microorganism, or by showing crossreactivity of isolated adhesins to the antibodies.

VIII. Vaccine Compositions

Also included in the invention is a vaccine composition containing an Exo S peptide and an immunogenic peptide carrier to which the peptide is bound. The composition is used as a vaccine against infection by microorganisms which have surface proteins which are antigenically crossreactive with antibodies produced against a C-terminal portion of Exo S and particularly the epitope formed by the sequence identified as SEQ ID No: 2 and characterized by (a) immunospecific binding to monoclonal antibody PK99H or MCA1; (b) a peptide length less than 20 amino acid residues; and (c) ability to block binding of Pseudomonas aeruginosa to buccal epithelial cells.

In one embodiment, the peptide includes the sequence identified as SEQ ID No: 2.

Particularly useful immunogenic carriers include keyhole limpet hemocyanin (KLH), tetanus toxoid, poly-L-(LYS:GLU), peanut agglutinin, poly-D-Lysine, diphtheria toxoid, ovalbumin, soybean agglutinin, bovine serum albumin (BSA), human serum albumin, and the like.

The peptide may be conjugated to the carrier by a variety of known methods, including chemical derivatization or by standard genetic engineering techniques (e.g., Ausubel).

Vaccines and inocula of the present invention may be administered by injection, usually intramuscularly or subcutaneously, orally by means of an enteric capsule or tablet, as a suppository, as a nasal spray, and by other suitable routes of administration. For a human patient, a suitable dose of the polypeptide depends, in part, upon the chosen route of administration and a number of other factors. Included among those factors are the body weight of the subject to be immunized, the carrier used, the adjuvant used, and the number of inoculations desired to be used.

Individual inoculations for a human patient typically contain unit doses of about 10 micrograms to about 100 milligrams of polypeptide, exclusive of any carrier to which the polypeptide may be linked. If desired, a series of doses may be administered over a period of time for optimum immunity. Unit dosage forms of the vaccine can also be provided, if desired, containing the aforementioned amounts of the polypeptide.

IX. Peptide Treatment

In one preferred mode of administration, peptides of the invention are delivered by nasal insufflation of powders or atomized solutions containing the peptide. This mode of administration has the advantage that delivery of the peptide is made directly to the pulmonary mucosal epithelial surface.

Yet another use of the peptides of the invention is as target molecules for drug delivery to pulmonary epithelial cells. Since the peptides bind specifically to epithelial cells, they are construed to be useful as therapeutic adjuvants in pathological conditions involving epithelial cells present in the lungs which are common targets of Pseudomonas and related pathogenic organisms. One such condition is carcinoma of the lung. In one preferred use, the peptides of the invention are conjugated to a photoactivatable chemotherapeutic agent useful in the treatment of lung carcinoma. The drug-peptide conjugate is then administered by nasal insufflation, and the drug is activated by high intensity light delivered through a bronchoscope.

The following examples illustrate methods for preparing and using the peptide and antibody of the invention. The examples are intended to illustrate, but not limit, the scope of the invention.

EXAMPLE 1

Purification of Exo S

Exo S was purified from *P. aeruginosa* strain DG1 by published methods (Woods 1987). The composition of the preparations used in the glycosphingolipid binding studies varied as some samples contained lipopolysaccharide. The preparation used in the adherence inhibition assays produced a single protein band on sodium dodecyl sulfate polyacrylamide gels (SDS-PAGE) as visualized by Coomassie blue staining.

EXAMPLE 2

DNA Sequence of Exo S

A. Cloning of Exo S

The gene for Exo S was cloned from *P. aeruginosa* strain DG1 using an oligonucleotide probe based on the partial N-terminal amino acid sequence to screen a library of DG1 SstI fragments inserted into pKT230 in *Escherichia coli* DH1 as described by Sokol et al (1990).

B. Sequencing of Structural gene for Exo S

The *P. aeruginosa* Exo S structural gene was sequenced by the Sanger dideoxy-chain termination method (Sanger, Tabor) as modified by using the Sequenase Kit (U.S. Biochemical Corp.) as described by the manufacturer. Overlapping clones were generated by the method of Dale (Dale). Sequence data were analyzed by using International Biotechnology Inc. software and the University of Wisconsin Computer Group software (Devereux).

EXAMPLE 3

Solid-Phase Synthesis of Pilin PAK and Exo S Peptides

Abbreviations used in this example are BOC, tertiary butoxycarbonyl; DCM, dichloromethane; TFA, trifluoroacetic acid; and BOC-AA-OH, amino acids protected at the alpha amino group by BOC group.

Commercially available phenylacetamidomethyl resin for polypeptide synthesis is obtained from Applied Biosystems (Foster City, Calif.). BOC-AA-OH were obtained from Institute Armand Frappier (Laval, Quebec, Canada). Side-chain protecting groups on the residues are as follows: o-(p-bromobenzoyloxycarbonyl) for tyrosine, o-benzyl for threonine, serine, aspartic acid and glutamic acid; S-methoxy-benzyl for cysteine, 2-chlorobenzyloxycarbonyl for lysine and formyl tryptophane.

A. Solid-phase Synthesis

In preparing a synthetic polypeptide of this invention by the above solid-phase method, the amino acid residues are linked to a resin (solid-phase) through an ester linkage from the carboxy-terminal residue.

Reactive amino acid side chains are also protected during synthesis of the polypeptide. Couplings are typically carried out using a 2-fold molar excess of protected amino acid and one equivalent of dicyclohexyl carbodiimide over the number of milliequivalents of initial N-terminal amino acid. For asparagine (N) and glutamine (Q), 2 molar equivalents of N-hydroxy-benzotriazole and dicyclohexyl carbodiimide were used. Coupling reactions are monitored by the ninhydrin test of Sarin (1981) and are typically more than 99% complete.

B. Oxidation and Purification of the Peptide

The peptide is cleaved from the resin and subsequently cyclized to form a disulfide bond. The cleavage of the peptide and the complete removal of the side-chain protecting groups is accomplished using anhydrous hydrogen fluoride. The resin is suspended in a mixture containing hydrogen fluoride and anisole (9:1, v/v) and the reaction is allowed to proceed in vacuo for 45 minutes at 5° C. The hydrogen fluoride is then evaporated. The resin is removed and washed with ether ($3 \times 10$ ml) and the peptide is extracted with 30% acetic acid ($3 \times 10$ ml). The combined filtrates are diluted to give a 5% aqueous acetic acid solution and lyophilized.

The crude peptide can be purified on an analytical reversed-phase HPLC column ($250 \times 4.6$ mm internal diameter) using a shallow gradient. The crude peptide is dissolved in the smallest volume of starting buffer possible (about 5 ml). The highly concentrated peptide is centrifuged to sediment undissolved material. An analytical sample, 5-10 µl, is chromatographed using a linear gradient (solvent A is 0.05% aqueous TFA and solvent B is 0.05% TFA in acetonitrile) to determine the total amount of peptide present. When the crude peptide contained hydrophilic and hydrophobic impurities with retention times close to that of the peptide of interest in the analytical run (1% B/min gradient rate), a shallow gradient of 0.2% B/min with a flow rate of 1 ml/min is employed.

The whole stock solution of 30–50 mg is injected onto the column and the run is monitored at 210 nm. Fractions (1 ml) are collected and analysed. Every third or fifth fraction is analysed to identify the region on the chromatogram with the peak of interest. Further analysis of the fractions within this region are then carried out. The chromatogram of each run can be compared with the initial analytical run prior to purification to ascertain the peak of interest. In this way, the shoulders of the neighboring peaks are eliminated, while fractions of interest are pooled and freeze dried. Dried peptides are stored in glass vial in a desiccator.

Mass spectrometry and HPLC anlysis are used to confirm the peptide structure.

EXAMPLE 4

Preparation of Antibodies

A. Polyclonal antibodies

Polyclonal antiserum to Exo S (anti-exo S) was raised in New Zealand rabbits was prepared as described previously (Woods 1987). Western blotting of with this antibody preparation revealed reactivity with Exo S and LPS. Therefore, antiserum used in gold labeling studies was absorbed with *P. aeruginosa* strain DG-ExS5, which is deficient in the production of Exo S (Woods 1985).

Polyclonal antiserum to PAK pili (anti-PAK) were prepared essentially as described above, using as antigen pili isolated from *P. aeruginosa* strain PAK, isolated as described by Paranchych (1979). Polyclonal antiserum to a specific sequence of PAK pilin protein (amino acid residues 128-144 of the purified protein; anti-PAK(1-28-144)$_{ox}$) was prepared using the peptide conjugated to keyhole limet hemocyanin as described in a previous publication (Lee, 1989).

B. Monoclonal Antibodies

Monoclonal antibodies against native PAK pili protein were prepared according to methods described elsewhere by the inventors (Doig). Briefly, BALB/c mice were immunized with weekly injections of PAK pili, which were isolated as described by Paranchych (1979). Spleen cells from the animals were fused with mouse myeloma cell line NS1 (Irvin), and successful fusions were screened by an ELISA method for ability to secrete anti-pilin antibody. A library of 262 hybridoma clones that secreted antibodies immunoreactive with PAK pili were obtained. Protein A purified Mabs were then screened against pilin peptide fragments (Doig), to determine specificities of these antibodies. Four hybridoma cell lines were selected for further specificity studies: cell lines PK99H, PH34C, PK3B, and PK41C.

Immunoblots of purified PAK and PAO pili revealed that PK99H and PK3B Mabs were specific for PAK pilin protein, while PK34C and PK41C Mabs were immunoreactive with both PAK and PAO pilin peptide. PK99H and PK34C Mabs were both immunoreactive with a C-terminal fragment of PAK pilin. Hybridoma cell lines PK99H and PK34C (Doig) were deposited in the cell depository of the Department of Medical and Infectious Diseases of the University of Alberta, Alberta, Canada, and are identified by cell line Nos. PK99H and PK34C.

Monoclonal antibodies to purified Exo S were prepared as published elsewhere by one of the inventors (Woods 1987). Briefly, a purified preparation of Exo S subjected to dialysis against 1% formalin in 0.1M Tris buffer (pH 8.0) and 0.2 M L-lysine, followed by dialysis against 0.2 M L-lysine in 0.85% NaCl, pH 6.3. BALB/c mice were injected intraperitoneally four times with 50 ug of the formalin-lysine treated Exo S on days 0, 7, 14, and 21. Three days after the final injection, mouse spleens were removed, and dispersed cells were fused with NS-1 cells using 50% (wt/wt) polyethylene glycol (MW 1500). Fused cells were transferred to microtiter dishes, and supernatants were tested for production of antibody to Exo S, using an ELISA procedure. Positive cell lines were subcloned extensively and were injected into pristane primed mice for ascitic tumor production. Antibodies present in ascitic fluid were purified on hydroxylapatite column, and immunoreactivity was verified using Western blots.

Monoclonal antibodies to Exo S were additionally tested for ability to a) inhibit enzyme (ADP ribosylation) activity and b) neutralize cytotoxic effects of Exo S, as described by Woods (1987). Monoclonal antibody MCA1 was found to have relatively low potency in inhibition enzyme activity and high potency in neutralization of cytotoxicity by Exo S. Monoclonal antibody MCA2 was found to have much greater potency in inhibition of enzyme activity, but relatively low potency in neutralizing the cytotoxic effects of Exo S. MCA2 was subsequently used in purification of the protein (Woods, 1987). Monoclonal antibody MCA3 was shown to neutralize cytotoxicity but not inhibit enzyme activity.

C. Immunogold Labeling and Immuno-electron Microscopy of PS Strain DG1

The antibody-gold-conjugate labelling procedure used was a modification of that described by Godfrey. Formvar coated electron microscope grids were coated with 0.1% bovine serum albumin in distilled water. A 5 $\mu$l suspension of PS strain DG1 was placed on the grids and allowed to settle for 5 min. Excess bacterial suspension was drained from the grids, and the grids were immediately floated over a drop of a solution containing a 1:10 dilution of anti-Exo S monoclonal antibody in PBS and incubated at 37° for 30 min. The grids were then washed three times by successive floating over drops of PBS (5 min each wash). The grids were then floated over a drop of anti-rabbit antibody gold conjugate (Sigma, St. Louis, Mo.) and incubated at 37° for 30 min. The grids were washed again as above, briefly rinsed in distilled water and examined (unstained) in a Phillips EM400 electron microscope.

FIGS. 2A and 2B show immunoelectron microscopy of P. aeruginosa cells exposed to monoclonal antibody raised against purified Exo S (2A) or phosphate buffered saline (2B followed by exposure to protein A-colloidal gold.

EXAMPLE 5

Binding to Buccal Epithelial Cells

A. Preparation of Buccal Epithelial Cells (BECs)

Buccal Epithelial Cells (BECs) were collected from ten healthy non-smoking male volunteers via wooden application sticks rubbed gently on the inside of cheeks, three wooden application sticks per cheek. These sticks were rubbed gently together in 30 mL phosphate buffered saline to suspend the BECs. These cells were washed three times with 30 mL phosphate buffered saline by successive centrifugation (650×g) and resuspended. The final pellet was suspended in 5 mL phosphate buffered saline at pH 7.2. This suspension was filtered (prewetted 70 $\mu$m nylon mesh) and the cells were diluted to a final concentration of $2 \times 10^5$ cells/mL in phosphate buffered saline at pH 7.2. This suspension was stored at 4° C. until ready for use.

B. Inhibition of Bacterial Adherence to BECs

The ability of purified Exo S, purified pili, and monoclonal antibodies to Exo S to inhibit binding of intact P. aeruginosa to buccal epithelial cells was examined as described by Woods (1980). Briefly, BECs were incubated with the test agent at 37° prior to addition of intact P. aeruginosa strain DG1. After incubation at 37° C. for 2 hours with shaking, the cells were washed, filtered, and the filters were assayed for the presence of bound bacteria.

C. Inhibition of Binding of Pili to BECs

Preparation of $F_{ab}$ fragments. $F_{ab}$ fragments of the PK99H and PK3B monoclonal antibodies, described above, and non-immune IgG were prepared using immobilized papain (Pierce Chemical Co., Rockford, Il). Briefly, affinity purified antibody was dialyzed against 20 mM cysteine HCl, 10 mM tetrasodium ethylenediaminetetraacetic acid (EDTA) in 20 mM sodium phosphate buffer pH 6.2. Antibody (1 ml containing approximately 2 mg antibody) was added to 0.5 ml immobilized papain and incubated at 37° C. for 20 h with shaking at 150 rpm. The immobilized papain was removed by centrifugation and the supernatant containing the Fab fragments was diluted with 1 ml of PBS.

The Fab fragments were purified by HPLC using a Protein G column eluted with PBS. Fab fragments were collected in the flowthrough, and Fc fragments were eluted from the column with 10 mM glycine pH 2.75. Fab fragments were concentrated by placing the Fab effluent in dialysis tubing (molecular weight cutoff of <8000) and extracting liquid from the dialysis sack using polyethylene glycol (molecular weight of 15,000-20,000). The fragments were then dialyzed against PBS. Activity of Fab fragments was checked by ELISA and production of Fab fragments was confirmed by SDS-PAGE.

PAK pili were isolated according to published procedures (Paranchych et al., 1979). Fab fragments of antibodies PK99H and PK3B, prepared as described above, were preincubated with PAK pili. The final concentration of PAK pili was 5 μg/ml. Pili binding was detected using monoclonal antibody PK3B (which is specific against pilin protein, but not the PAK peptide). All Fabs were diluted such that their final titre as measured by ELISA to PAK pili was $10^{-3}$.

Pili binding, as measured by enzyme activity associated with BECs, is expressed as percent control (no Fab fragments added).

EXAMPLE 6

Antibody Cross-reactivity

A. Direct ELISA Experiments

Antigens were coated on NUNC 96-well polystyrene wells. Antigen (10 ug/mL in 0.01M carbonate buffer, pH 9.5) was added to each well (100 μl/well) and left for 6 h at room temperature. Wells were then washed 3 times with 250 μl of PBS pH 7.4 supplemented with 0.02% (wt/vol) BSA (buffer A). Wells were blocked with 5% (wt/vol) BSA in PBS pH 7.4 overnight at 4° C. Wells were washed three times and 100 μl of primary antibody was added for 2 h. Each well was then washed 3 times with 250 μl buffer A using aspiration. A goat anti-mouse IgG (H+L) immunoglobulin-horse radish peroxidase conjugate (Jackson Laboratories) in buffer A (100 μl/well) was added and incubated for 2 h at room temperature. The wells were washed 3 times with buffer A and 250 51/well substrate solution (1 mM 2,2'-azino-di-(3-ethylbenzthiazoline sulfonic acid), 0.03% (vol/vol) hydrogen peroxide in 10 mM sodium citrate buffer pH 4.2) added. The reaction was stopped by the addition of 250 μ/well of 4 mM sodium azide and absorbance at 405 nm determined using an EL-407 plate reader.

Table 3 shows results of experiments using test antigens pili from *P. aeruginosa* strains PAK, PAO, and P1, as well as Exo S (Exo S) and the PAK pilus peptide PAK $(128-144)_{ox}$. Serial dilutions of test monoclonal or polyclonal antibodies prepared against pili, specific peptides of pili, or Exo S were tested for binding to these antigens. Reciprocals of the titers shown in Table 3 indicate the highest dilution of test antibody solution at which binding to the antigen in the plate was detected.

B. Competitive ELISA experiments

Competitor and antibody were mixed together in 10 mM PBS pH 7.2 buffer containing 0.05% (w/v) BSA and incubated for 30 min at room temperature. The conditions of the assay were such that less than 50% of the antigen immobilized on the ELISA plate surface would be bound with antibody if there was no competitor present. The mixture of antibody and competitor was then added to wells (100 μl/well) coated with PAK pili fimbriae and blocked with BSA as described above. The ELISA was then performed as described above.

Figure 4B:
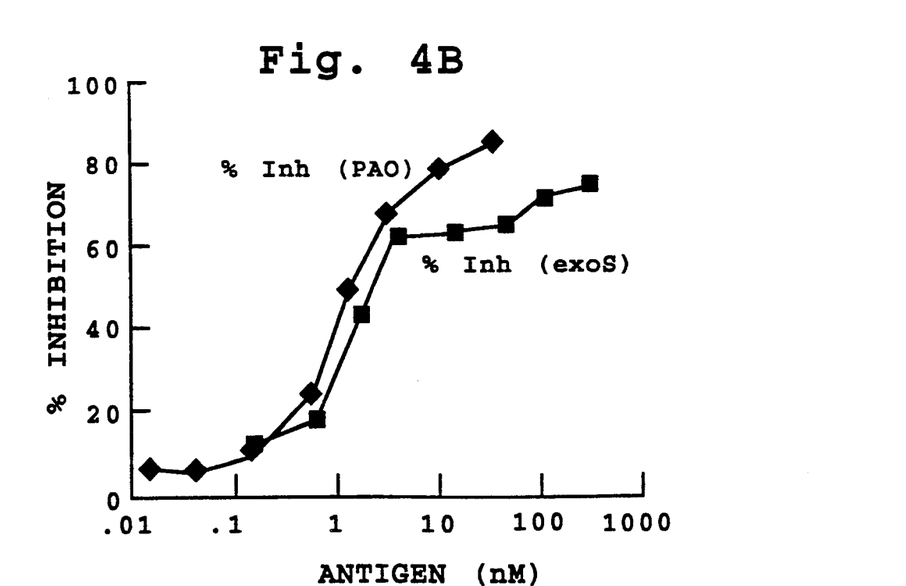
Figure 5:
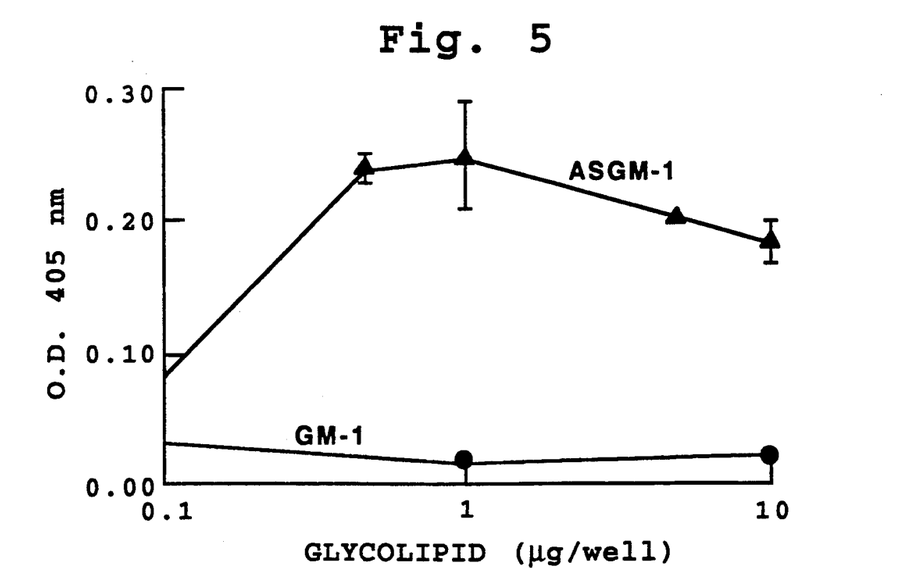
FIG. 5 shows a plot of binding of purified Exo S to glycosphingolipids.

FIGS. 4A and 4B and 5 show the results of experiments in which PAK pili, PAO pili or Exo S were coated onto ELISA plates at a concentration of 1 μg/ml. Wells were then blocked with excess non-reactive protein solution and washed to remove unbound materials. Polyclonal anti-Exo S antibody (Woods 1987) was then added to the wells. Competition between test agent and the anti-Exo S antibody was effected by pre-mixing the test agent and the antibody for 30 minutes at room temperature prior to adding the mixture to the antigen coated wells. After incubation of the anti-Exo S in the presence of test agent in the coated wells, the plates were washed, then reacted with alkaline phosphatase-linked second antibody, to quantitate binding of anti-Exo S to the coated wells.

EXAMPLE 7

Binding to Glycosphingolioids

A. Glycosphingolipids Thin Layer Chromatography (TLC) Binding Assay

Purified glycosphingolipids (GSLs) were purchased from Sigma Chemical Co. (St. Louis, Mo.). The total non-acid glycosphingolipid fraction from dog intestinal mucosa, a gift from G. Hansson, University of Goteborg, Boteborg, Sweden, was described previously (Hansson). The TLC plate binding assay was carried out using modified methods (Baker).

Glycosphingolipids (ganglio-tetraosyl ceramide, $GM_1$, and neutral GSLs of dog mucossa were separated on aluminum-backed silica gel Si50 HPTLC plates in chloroform-methanol-water (60:35:8). One plate was sprayed with cupric acetate for chemical detection and duplicate plates were used for bacterial or Exo S binding assays. The TLC plates were immersed in 0.3% polyisobutylmethacrylate in diethylether-hexane (1:1) for 1 min and air dried. Plates were wet with phosphate buffer saline (PBS) containing 0.2% Tween TM (PBS-T) and overlaid with 2 to 3 ml of Exo S diluted in PBS-T or a suspension of *P. aeruginosa* strain DG1 diluted to $O.D._{600}$ of 0.5 in PBS-T. After a 2-h incubation at room temperature, the plates were washed 5 to 6 times with PBS-T. Bound Exo S or bacteria were detected by sequential 1-h overlays with 2 to 3 ml of 1:1000 dilutions of anti-Exo S and alkaline phosphatase labeled goat-anti-rabbit IgG in PBS-T. After the final incubation, the plates were washed 3 times with PBS-T and 2 times with 0.05M Tris-saline, pH 7.4. The plates were developed by immersion in Tris-saline containing 2 mg of Fast Red and 1 mg of naphthol phosphate per ml. Plates were observed for development of a red precipitate. (FIG. 6).

B. Solid Phase Binding Assay (1) Binding of Exo S to GSLs

Glycosphingolipids were diluted in methanol, and 25-μl aliquots were added to individual wells of 96-well microtiter plates. The plates were dried slowly overnight at room temperature, rinsed once with PBS-T, and 50 μl of test agent diluted in PBS was added to each well (10 μg protein/well). The plates were incubated for 2 h at room temperature and rinsed 4 to 5 times with PBS. Bound Exo S was detected by sequential addition of 50 μl of anti-Exo S and alkaline phosphatase-conjugated goat-anti-rabbit IgG with intermittent and final washes with PBS-T. The plates were developed by addition of 100 μl of 1 mg of nitrophenol phosphate in 10% diethanolamine buffer (pH 9.6). The plates were read at 405 nm. (FIG. 8 shows exoS as test agent; FIGS. 9 A-D smf FIG. 10 show the results of studies in which PAK pili were tested for immunoreactivity; Table 3 summarizes these data)

(2) Binding of Pili to GSLs

The binding of PAK Pili, PAO pili and exoenzyme S to the glycolipids asialo-GM1 and GM1 was determined by a modified ELISA type assay. The glycolipid (after purity was verified by TLC analysis with authentic standards) was coated on ELISA plates by dissolving the glycolipids in 10% (v/v) chloroform in methanol to a concentration of 1 mg/ml and diluting the glycolipids in methanol to obtain the appropriate concentration, a 100 μl of the glycolipids in methanol was added to each well and allowed to evaporate to dryness at 4° C. The wells were then blocked by the addition of 100 μl/well of 5% (w/v) BSA in PBS pH 7.2 for 1 hour at 37° C. Wells were washed 5 times with 250 μl/well of 0.05% (w/v) BSA in PBS pH 7.2. Pili or exoenzyme S in 0.5% (w/v) BSA in PBS pH 7.2 were then added (100 μg/well) and incubated for 1 hour at 37° C. Wells were then washed 5 times with 250 μl well of 0.05% (w/v) BSA in PBS pH 7.2. The appropriate antibody (PK3B for PAK pili, polyclonal anti-PAO pili for PAO pili, and polyclonal anti-exoenzyme S antibody for exoenzyme S) was then added (100 μl/well) and incubated at 37° C. for 1 hour. Wells were then washed 5 times with 250 μl/well antibody-enzyme conjugate (anti-mouse IgG-HRP conjugate for PK3B and anti-rabbit IgG-alkaline phosphatase conjugate for the polyclonal antibodies). Wells were then washed 5 times with 250 μl/well of 0.05% (w/v) BSA in PBS pH 7.2. The appropriate substrate was then added and the optical density at 405 nm was then determined after the reaction had been stopped.

C. Inhibition of PAK pili binding to GalNAcGal-BSA

Test agents were tested for ability to inhibit binding to GSL conjugated to bovine serum albumin (BSA).

Although preferred embodiments of the invention are described herein in detail, it will be understood by those skilled in the art that variations may be made thereto without departing from the spirit of the invention or the scope of the appended claims.

It is claimed:

1. An exo S peptide consisting of the sequence CATTATGPNGSC identified by Seq. ID. No. 2, and having a peptide length less than 20 amino acid residues.

2. The peptide of claim 1, wherein the two terminal cysteine (c) residues in the sequence are linked covalently.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 36 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( A ) ORGANISM: Pseudomonas aeruginosa
( C ) INDIVIDUAL ISOLATE: sequence derived from Exoenzyme S coding sequence ( x i ) SEQUENCE DESCRIPTION: SEQ ID NO:1:

TGCGCGACTA CCGCTACTGG CCCGAATGGC AGTTCG           3

( 2 ) INFORMATION FOR SEQ ID NO:2:

( i ) SEQUENCE CHARACTERISTICS:
( A ) LENGTH: 12 amino acids
( B ) TYPE: amino acid
( D ) TOPOLOGY: both ( i i ) MOLECULE TYPE: peptide ( i i i ) HYPOTHETICAL: NO ( v ) FRAGMENT TYPE: N-terminal ( v i ) ORIGINAL SOURCE:
( A ) ORGANISM: Pseudomonas aeruginosa
( C ) INDIVIDUAL ISOLATE: peptide from Exoenzyme S ( x i ) SEQUENCE DESCRIPTION: SEQ ID NO:2:

Cys Ala Thr Thr Ala Thr Gly Pro Asn Gly Ser Cys
1               5                   10